(12) United States Patent
Hoffa (10) Patent No.: US 8,100,881 B2
(45) Date of Patent: Jan. 24, 2012

(54) FLEXIBLE MEDICAL DEVICE FOR CLOT REMOVAL FROM SMALL VESSELS

(75) Inventor: Andrew K. Hoffa, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 121 days.

(21) Appl. No.: 12/535,229

(22) Filed: Aug. 4, 2009

(65) Prior Publication Data

US 2011/0034863 A1 Feb. 10, 2011

(51) Int. Cl.
*A61M 25/00* (2006.01)
(52) U.S. Cl. ........................................ 604/524; 604/526
(58) Field of Classification Search .......... 604/524–527, 604/523, 529, 164.13; 600/585
See application file for complete search history.

(56) References Cited

U.S. PATENT DOCUMENTS

| | | | |
|---|---|---|---|
| 4,932,419 A | 6/1990 | de Toledo | |
| 5,290,230 A | 3/1994 | Ainsworth et al. | |
| 5,601,539 A | 2/1997 | Corso, Jr. | |
| 5,769,830 A | 6/1998 | Parker | |
| 5,891,090 A | 4/1999 | Thornton | |
| 6,193,686 B1 | 2/2001 | Estrada et al. | |
| 6,306,124 B1 | 10/2001 | Jones et al. | |
| 6,524,300 B2 | 2/2003 | Meglin | |
| 6,530,935 B2 | 3/2003 | Wensel et al. | |
| 6,589,227 B2 | 7/2003 | Sønderskov Klint | |
| 6,818,001 B2 | 11/2004 | Wulfman et al. | |
| 6,881,194 B2 | 4/2005 | Miyata et al. | |
| 7,020,947 B2 | 4/2006 | Bradley | |
| 7,100,891 B2 | 9/2006 | Doyle | |
| 7,117,703 B2 | 10/2006 | Kato et al. | |
| 7,182,757 B2 | 2/2007 | Miyata et al. | |
| 7,501,579 B2 | 3/2009 | Michael et al. | |
| 2001/0016728 A1 | 8/2001 | Kelley | |
| 2002/0139785 A1 | 10/2002 | Peacock, III et al. | |

(Continued)

FOREIGN PATENT DOCUMENTS

EP 0 806 596 A1 11/1997

(Continued)

OTHER PUBLICATIONS

Article entitled "Helical Hollow Strand," Fort Wayne Metals, www.fwmetals.com, pp. 6.4-6.5.

(Continued)

*Primary Examiner* — Jackie Ho
*Assistant Examiner* — Deanna K Hall
(74) *Attorney, Agent, or Firm* — Brinks Hofer Gilson & Lione (57) ABSTRACT

A medical device and method of applying said medical device to deliver drugs and to remove thrombus or soft tissue clots from vascular or other lumens in a patient is presented. The medical device generally comprises an elongated tubular delivery member having a proximal portion and a distal portion that differ in rigidity and a leak-free connector that is in contact with the proximal portion of the delivery member and is compatible for use with fibrinolytic agents and application of a vacuum. The delivery member includes a metal core made out of multiple shaped-wire strands and a polymer overlay disposed about the core. The wire strands, which have both an A-side and a B-side, are helically wound to form a polygonal shaped lumen whose inner diameter is defined by the A-side of the strands.

20 Claims, 4 Drawing Sheets

U.S. PATENT DOCUMENTS

| | | | |
|---|---|---|---|
| 2002/0198492 A1 | 12/2002 | Miller et al. | |
| 2004/0087968 A1 | 5/2004 | Core | |
| 2004/0153110 A1 | 8/2004 | Kurz et al. | |
| 2004/0181207 A1 | 9/2004 | Vitullo et al. | |
| 2006/0095018 A1 | 5/2006 | Pursley | |
| 2006/0100602 A1 | 5/2006 | Klint | |
| 2006/0111649 A1* | 5/2006 | Zhou | 600/585 |
| 2006/0200074 A1 | 9/2006 | Zadno-Azizi | |
| 2007/0016233 A1 | 1/2007 | Ferrera et al. | |
| 2008/0045881 A1 | 2/2008 | Teitelbaum et al. | |
| 2008/0065045 A1 | 3/2008 | von Hoffmann | |
| 2009/0054826 A1 | 2/2009 | Hoffa | |

FOREIGN PATENT DOCUMENTS

| | | |
|---|---|---|
| WO | WO 2006/020044 A1 | 2/2006 |
| WO | WO 2006/055201 A1 | 5/2006 |

OTHER PUBLICATIONS

Ron Roth, Article entitled "Design Considerations in Small-Diameter Medical Tubing," Medical Device & Diagnostic Industry Magazine, www.medicaldevicelink.com, Jan. 2001, 6 pages.

Article entitled "Biomedical Coatings," Fort Wayne Metals, www.fwmetals.com, pp. 7.1-8.1.

CA Jungreis, et al., Article entitled "Intracranial thrombolysis via a catheter embedded in the given clot," Journal of the American Heart Association, http://stroke.aha.journals.org, 1989, pp. 1578-1580.

Joseph M. Eskridge, M.D., et al., Article entitled "Catheter-Related Thrombosis and Fibrinolytic Therapy," Radiology, Nov. 1983, pp. 429-432.

L D R Smith, et al., Article entitled "Use of a hollow wire to facilitate angioplasty of occluded vessels," Br Heart J 1989;61, pp. 326-330.

Article entitled "Shaped Wire," Fort Wayne Metals, www.fwmetals.com, p. 6.2.

A. Pusz, K. Michalik Article entitled "Examining the hardness of the high density polyethylene with method of the cone," Archives of Materials Science and Engineering, www.archivesmse.org, vol. 28, Issue 8, Aug. 200, pp. 467-470.

Muharrem Aktümen, et al., Article entitled "The Method Using Regular Polygons," The Journal of the Online Mathematics and Its Applications, http://www.maa.org/joma/Volume7/Aktumen/Polygon.html, vol. 7, 2007, 5 pages.

Dan Ismailescu, Article entitled "Circumscribed Polygons of Small Area," Springer Science+Business Media, LLC, Feb. 27, 2008, 7 pages.

Article entitled "Trigonometric Formulas and Relationships," http://ca.geocities.com/xpf51/ANGLE_FORMULAS/TRIG_FORMULAS.html, 2 pages.

* cited by examiner

FLEXIBLE MEDICAL DEVICE FOR CLOT REMOVAL FROM SMALL VESSELS

FIELD

This invention relates generally to medical devices used in the vasculature of a patient and more particularly to devices used to deliver drugs and to remove thrombus or soft tissue clots from vascular or other lumens in a patient.

BACKGROUND

Since small vessel emboli (e.g., intracranial clots) are usually difficult to remove mechanically due to the limited size of the vessel, catheter-directed fibrinolysis is frequently considered to be the best available treatment. The goal associated with catheter-directed fibrinolysis is to deliver a fibrinolytic agent directly to a thrombus in order to activate the plasminogen bound to the fibrin clot. In order to achieve this goal, an infusion catheter or wire is typically embedded within the thrombus and a fibrinolytic agent, such as a tissue-type plasminogen activator (t-PA), is continuously infused through the catheter at a rate of 1-2 mg per hour until successful dissolution of the thrombus is achieved between 12-18 hours later.

One problem routinely encountered during such catheter-directed fibrinolysis is pericatheter thrombosis. Pericatheter thrombosis results from poor blood flow along the length of the catheter. In order to decrease the incidence of this problem, a low dosage of intravenous heparin (500-1000 units/hr) is frequently introduced into the vessel through the catheter's sheath. Anticoagulation with heparin is also known to be helpful to prevent rebound thrombosis after the fibrinolytic infusion is completed. Additional methods used to reduce the occurrence of pericatheter thrombosis is to keep the intravascular length of catheter to a minimum, to use a catheter with the smallest possible diameter, and to reduce the overall length of time associated with the infusion.

An additional complication that can be encountered during catheter-directed fibrinolysis is related to the occurrence of bleeding at the arterial puncture site. This type of complication is usually considered minor, but can be life threatening if it occurs at a remote site (i.e., intracranial, etc.). The risk associated with the occurrence of this complication is known to increase with the length of time associated with the infusion.

Accordingly, there exists a need to reduce the risks associated with catheter-directed fibrinolysis in small vessels. In particular, there exists a need to deliver the necessary dosage of fibrinolytic agent to achieve complete dissolution of the emboli over the shortest duration of time, while maintaining the minimum necessary diameter and length for the catheter used for the infusion.

SUMMARY

The present invention provides a medical device for clot removal from small vessels by fibrinolytic infusion or vacuum retrieval. One embodiment of a medical device, constructed in accordance with the teachings of the present invention, generally comprises an elongated tubular delivery member having a proximal portion and a distal portion and a leak-free connector that is in contact with the proximal portion of the delivery member and is compatible for use with fibrinolytic agents and application of a vacuum.

The delivery member is comprised of a metal core made out of multiple shaped-wire strands and a polymer overlay disposed about the metal core. The wire strands, which have both an A-side and a B-side, are helically wound to form a lumen whose inner diameter is defined by the A-side of the strands.

Geometrically, the helically wound wire strands form a first polygon defined by the B-side of the strands and a second polygon defined by the A-side of the strands. The second polygon defines the shape of the delivery member's lumen. The first polygon is further defined to inscribe a first circle having a radius, $R_1$, and the second polygon circumscribes a second circle having radius, $R_2$. The difference in magnitude between $R_1$ and $R_2$ is about equal to the thickness of the wire strands. The ratio of the area (A1) of the first polygon to the area (A2) of the second polygon is about equal to the quotient of $[(R_1)^2 \cdot \cos^2(\pi/N)]/(R_2)^2$, where N is the number of wire strands.

Another aspect of the delivery member of the present invention divides said member into proximal and distal portions with each portion being different in their predetermined degree of rigidity. The difference in rigidity between the proximal and distal portions can result from a variation in one of the wall thickness of the metal core, the hardness of the overlay, and a combination thereof. The variation in wall thickness of the core may result from a grinding operation being performed on the outer diameter of the corers distal portion. The variation in wall thickness of the hollow core may also result from using at least one different core for the proximal portion and the distal portion that have substantially similar inner diameters, but different outer diameters.

Another objective of the present invention is to provide a method for clot removal from small vessels by fibrinolytic infusion or vacuum retrieval. This method comprises the steps of introducing a sheath having a lumen into a blood vessel; inserting a guide wire through the lumen of the sheath; deploying the elongated tubular delivery member of the medical device of the present invention; positioning the distal end of the delivery member of the medical device proximate to a clot; removing the guide wire; injecting a fibrinolytic agent into the blood vessel through the delivery member until the clot is dissolved; and removing the delivery member of the medical device from the blood vessel. The method may further comprise the steps of applying a vacuum through the delivery member to a clot that is only partially dissolved and removing the partially dissolved clot via the vacuum.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

The following description is merely exemplary in nature and is in no way intended to limit the present disclosure or its application or uses. It should be understood that throughout the description and drawings, corresponding reference numerals indicate like or corresponding parts and features.

Figure 1:
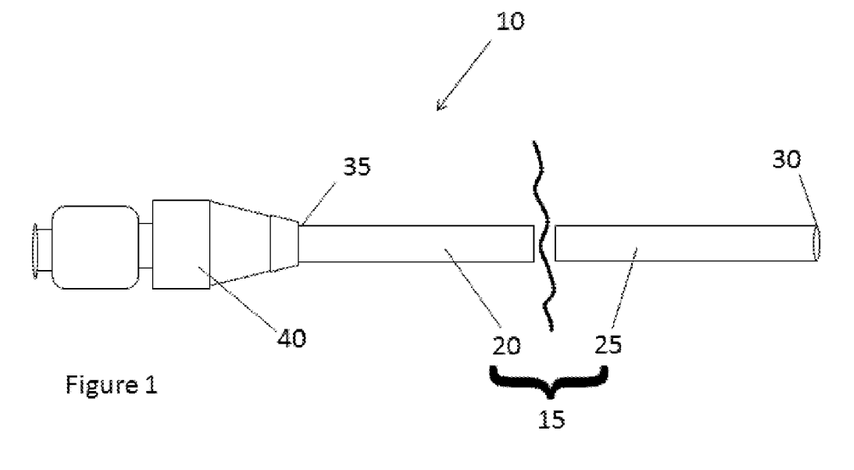
FIG. 1 is a perspective view of a medical device used for removal of a clot from a patient's vasculature having a delivery member and a leak-free connector according to the teachings of the present invention.

Referring to FIG. 1 a medical device 10 for intracranial clot removal according to the present invention is shown having a distal end 30, an elongated tubular delivery member 15 extending from the distal end 30 to a proximal end 35. The delivery member 15 has both a proximal portion 20 and a distal portion 25 with the proximal portion 20 being in contact with a leak-free connector 40 that is compatible for use with fibrinolytic infusion, vacuum retrieval methodology, or both. The proximal portion 20 and the distal portion 25 of the delivery member 15 may be different in their predetermined degree of rigidity.

Figure 2:
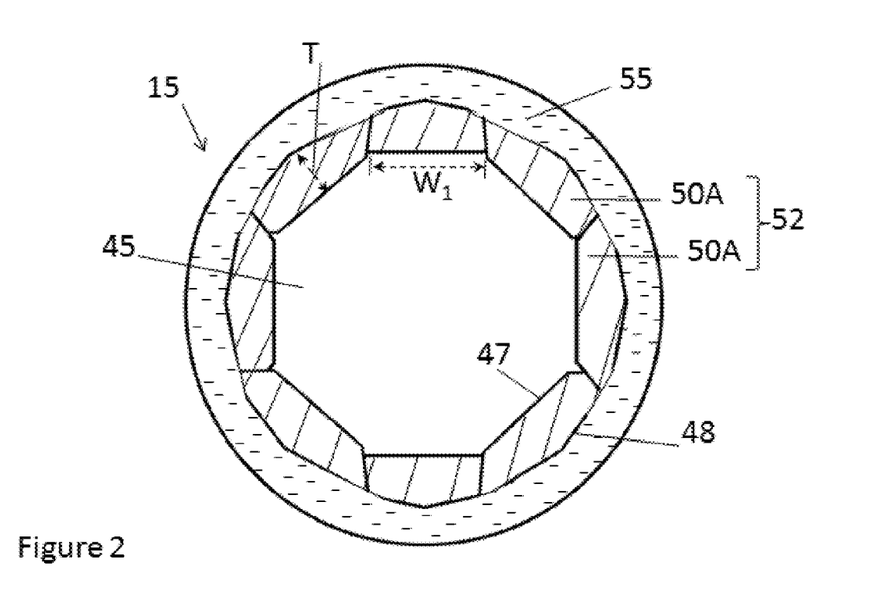
FIG. 2 is an axial cross-sectional view of the delivery member used in the medical device of FIG. 1 according to one aspect of the present invention.

Referring now to FIG. 2, the delivery member 15 is comprised of a metal core 52 of helically wound multiple wire strands 50A. Each wire strand 50A has an A-side 47 and a B-side 48 with the A-side 47 of the combined strands 50A forming a central longitudinally extending lumen 45. Each of the metal strands has a width and thickness defined as $W_1$ and T, respectively. A polymer overlay 55 is disposed about the metal core 52 or about the B-side 48 of the wire strands 50A. The helically wound wire strands 50A geometrically form a first polygon defined by the B-side 48 of the strands 50A and a second polygon defined by the A-side 47 of the strands 50A.

Figure 3:
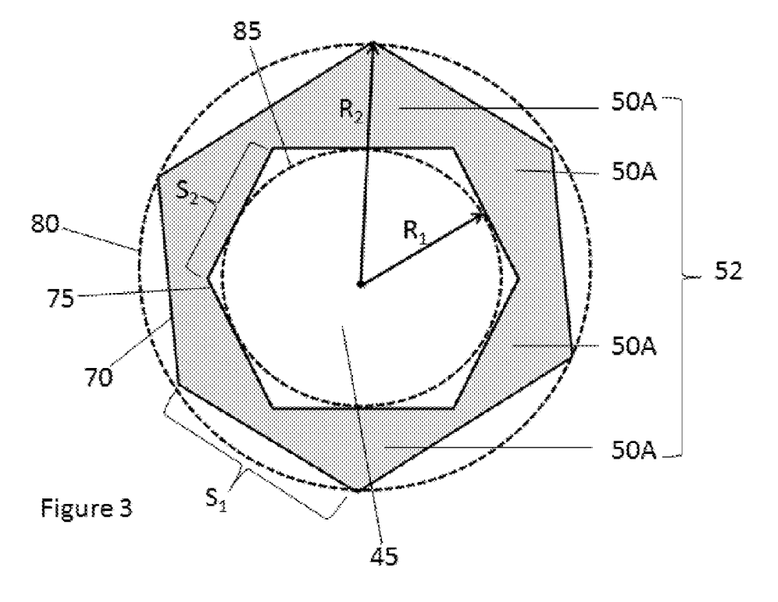
FIG. 3 is a geometric representation of the cross-sectional area of the delivery member used in the medical device of FIG. 1 according to one aspect of the present invention.

In FIG. 3, the geometry associated with the metal core 52 is further described. The B-side 48 and the A-side 47 of the helically wound wire strands 50A form a first polygon 70 and a second polygon 75, respectively, with the second polygon defining the shape of the lumen 45 of the metal core 52. The polygonal shape of the lumen 45 is preferable in order to maintain a wide open working channel or lumen through which a fibrinolytic agent may be delivered to a clot or thrombus. This wide open channel or lumen allows for the fibrinolytic agent to be effectively delivered in the shortest amount of time.

The first polygon 70 can be shown to inscribe a first circle 80, while the second polygon 75 is shown to circumscribe a second circle 85, respectively. The first circle 80 may further be defined as having a radius, $R_1$. The inscribed first polygon 70 may be defined by N-sides ($S_1$) with the length of each side being further described by the relationship shown in Equation 1. The second circle 85 may further be defined as having a radius, $R_2$. The circumscribed second polygon 75 may be defined by N-sides ($S_2$) with the length of each side being further described by the relationship provided in Equation 2. In Equations 1 and 2, N represents the number of wire strands 50A used to form the wire core 52. The difference between $R_1$ and $R_2$ is due to the thickness (T) associated with the wire strands 50A.

$$S_1 \approx 2 \cdot (R_1) \cdot \sin(\pi/N) \qquad \text{Eq. 1}$$

$$S_2 \approx 2 \cdot (R_2) \cdot \tan(\pi/N) \qquad \text{Eq. 2}$$

The cross-sectional area ($A_1$) of the first polygon 70 can be described by the relationship depicted in Equation 3. Similarly, the cross-sectional area ($A_2$) of the second polygon 75 can be described by the relationship shown in Equation 4. Upon combining Equations 1 and 2 with Equations 3 and 4, respectively, followed by trigonometric reduction using the known fundamental identity for $\tan(x)=\sin(x)/\cos(x)$, the ratio of the area ($A_1$) of the first polygon 70 to the area ($A_2$) of the second polygon 75 is derived to be about equivalent to the relationship provided in Equation 5. The polygonal shape of the metal core 52 provides for a cross-sectional area ($A_2$) of the lumen 45 formed therein to be greater than the circular cross-sectional area of a lumen formed by conventional helical wire winding that has a radius equivalent to $R_1$.

$$A_1 \approx [N \cdot (S_1)^2]/[4 \cdot \tan(\pi/N)] \qquad \text{Eq. 3}$$

$$A_2 \approx [N \cdot (S_2)^2]/[4 \cdot \tan(\pi/N)] \qquad \text{Eq. 4}$$

$$A_1/A_2 \approx [(R_1)^2 \cdot \cos^2(\pi/N)]/(R_2)^2 \qquad \text{Eq. 5}$$

Figure 4:
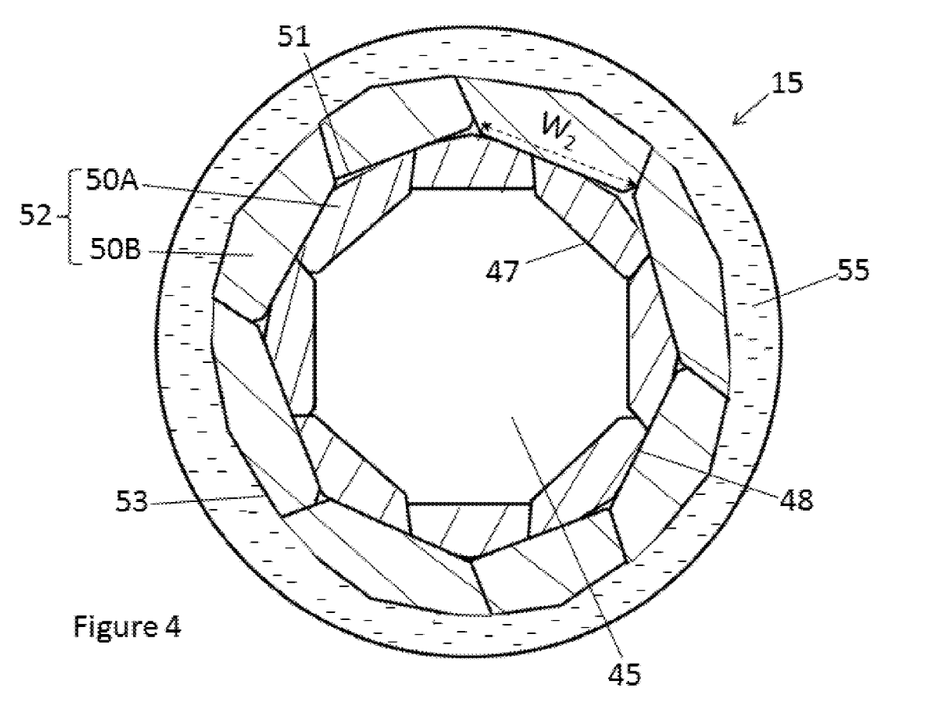
FIG. 4 is an axial cross-sectional view of the delivery member of the medical device of FIG. 1 according to another aspect of the present invention.
Figure 5A:
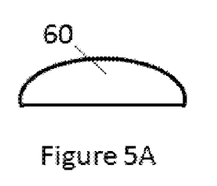
FIG. 5A is a cross-sectional view of a wire strand having a half-round shape according to one aspect of the present invention.
Figure 5B:
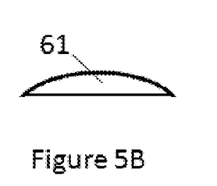
FIG. 5B is a cross-sectional view of a wire strand having less than half-round shape according to another aspect of the present invention.
Figure 5C:
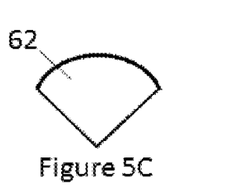
FIG. 5C is a cross-sectional view of a wire strand having pie shape according to another aspect of the present invention.
Figure 5D:
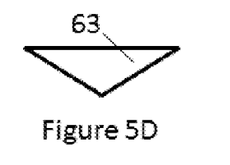
FIG. 5D is a cross-sectional view of a wire strand having a triangular shape according to another aspect of the present invention.
Figure 5E:
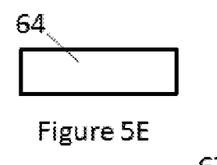
FIG. 5E is a cross-sectional view of a wire strand having a rectangular shape according to another aspect of the present invention.
Figure 5F:
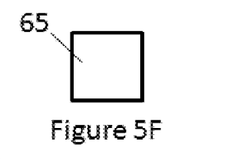
FIG. 5F is a cross-sectional view of a wire strand having a square shape according to another aspect of the present invention.
Figure 5G:
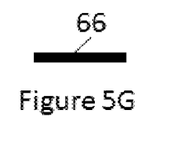
FIG. 5G is a cross-sectional view of a wire strand having flat shape according to another aspect of the present invention.
Figure 5H:
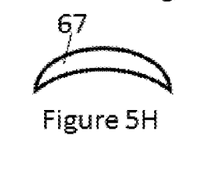
FIG. 5H is a cross-sectional view of a wire strand having half moon shape according to another aspect of the present invention.

Referring now to FIG. 4, the delivery member 15 may further comprise a second layer of helically wound multiple wire strands 50B where the A-side 51 of the wire strands 50B of this second layer are disposed about the B-side 48 of the first layer of helically wound wire strands 50A. Although this second layer of wire strands 50B is similar to the first layer of wire strands 50A in the number of strands, it differs in that the width ($W_2$) of each strand in the second layer is larger than the width ($W_1$) of each strand in the first layer. Although the use of a second layer of wire strands 50B can enhance the impermeability of the delivery member 15, it also may reduce the flexibility of the delivery member 15. When a second layer is used as part of the metal core 52 the polymer overlay is disposed about the B-side 53 of the wire strands 50B.

The delivery member 15 of the medical device 10 may be a catheter that is normally open ended at both the proximal 35 and the distal end 30. Such a catheter can be used for the intracranial removal of a clot after subjecting said clot to fibrinolytic infusion and/or assisting the removal of the clot through the application of a vacuum. One skilled-in-the-art will recognize that the medical device 10 of the present invention may be useful in a variety of other applications, including but not limited to percutaneous transluminal coronary angioplasty, drug delivery, and as a guiding catheter.

The wire strands 50A that are helically wound into the metal core 52 may be comprised of any linear elastic material, including but not limited to stainless steel platinum alloys, titanium, tantalum, or a superelastic alloy, such as nitinol. Preferably, the wire strands 50A have a tensile strength in the range of 1800 to 2700 N/mm$^2$ but lower or higher values are also possible. The metal core 52 of the delivery member 15 may be made by winding the metal strands 50A according to any method known to one skilled-in-the-art. For example, a group of about five to twelve wire strands 50A having the desired wire diameter may be placed in a row next to or closely adjacent to each other. The wire strands 50A are then wound according to the desired pitch angle into an elongated, tubular metal core 52. Because a row of wires is wound, each individual wire strand 50A is restricted in movement by the other wire strands 50A and is plastically deformed into a permanent helical shape which is kept without any further restraints other than each wire assists in keeping the other wires aligned in the row. The helical winding of the strands 50A forms a lumen 45 defined by the A-side 47 of the strands 50A.

After being helically wound, the coiled wire strands 50A can be subjected to heat treatment or drawing in order to further define the tubular structure and to reduce the presence of any residual stresses. For example, such a heat treatment may be performed over a period of about two to twenty hours at a temperature between about 400 to 600° C. The wire strands 50A in the resulting helically wound metal core 52 will maintain their position even when heavy torque is applied and the metal core 52 is bent or pushed in a specific direction. Such resiliency results presumably because each single wire strand 50A is supported by the other contiguous wire strands 50A in the wound metal core 52.

Figure 6:
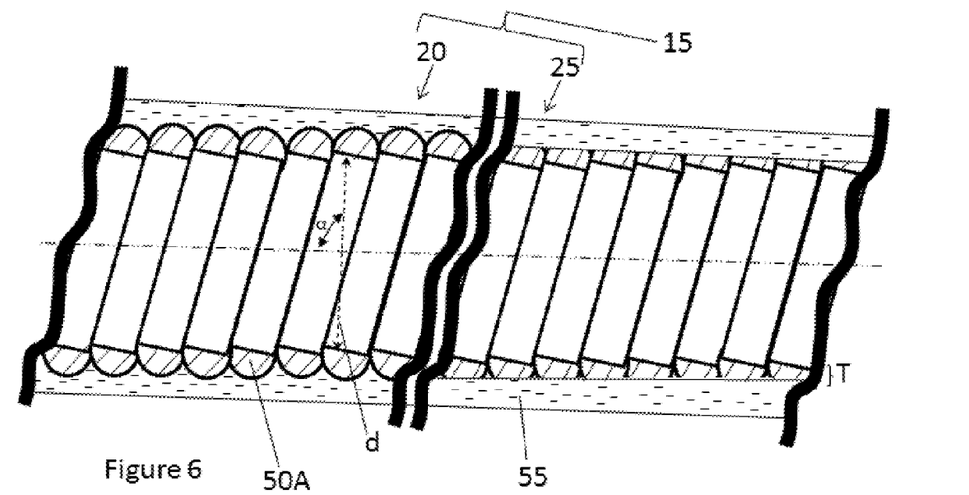
FIG. 6 is a longitudinal cross-sectional view of the delivery member of the medical device of FIG. 1 according to yet another aspect of the present invention.

The size of the pitch angle ($\alpha$) as defined in FIG. 6 depends on the width of the wire strands 50A, the diameter of the desired lumen 45 and the number of wire strands 50A used to form the metal core 52. The most preferred pitch angle for a catheter is in the range of 40° to 70° with the specific angle being determined by the desired balance in the metal core 52 between torque transferability and transverse flexibility. The width ($w_1$) of the individual wire strands 50A is typically in the range of about 0.10 to 1.25 mm, and preferably in the range of 0.15 to 0.50 mm. The present invention includes providing a medical device having different segments wherein the row of wires is set to different pitch angles, or wherein different rows of wires have different pitch angles.

Referring now to FIGS. 5A-5H, each wire strand 50(A, B) is a type of shaped wire with the shape being selected as one from the group of half round shaped D-wire 60, less than half round shaped D-wire 61, pie angle shaped wire 62 with greater than about a 90° degree angle, triangular shaped wire 63 having an obtuse angle, rectangular shaped wire 64, square shaped wire 65, flat shaped wire 66, crescent shaped wire 67, and combinations thereof. Preferably, the shaped wire is one selected from the group of half-round 60 shaped wire, less than half-round 61 shaped wire, triangular 63 shaped wire, rectangular 64 shaped wire, and combinations thereof.

A polymer overlay 55 is disposed about the wound wire strands 50A that form the metal core 52. The polymer overlay 55 is provided on to the B-side 48, 53 of the wire strands 50A, 50B or the external surface of the metal core 52. The polymer overlay 55 may be a material coated onto the outer surface of the core 52, a material extruded around the core 52, or a shrink tubing material that is pushed over the core 52. The polymer overlay 55 is preferably a thin layer of an elastic material that extends along the entire length of the delivery member 15. Preferably the polymer overlay 55 will reduce the tendency of the delivery member 15 to stick to the vascular wall. The polymer overlay 55 is typically applied after the winding and heat treatment of the metal core 52 has been completed. For example, the polymer overlay 55 may be a PTFE coating applied onto the external surface of the metal core 52 in the same manner as such a coating is traditionally applied onto the exterior of a guide wire. The polymer overlay 55 as disposed about the metal core 52, i.e., on the B-side 48 of the metal strands 50A, results in less than about a 5 to 15% increase in the outer diameter of the delivery member 15.

The composition of the polymer overlay 55 may include, but not be limited to, fluoropolymers, hyrdrophilic elastomers, polyolefins, and combinations or mixtures thereof. Several examples of fluoropolymers include ethylene-tetrafluoroethylene (ETFE), perfluroralkoxyethylene-tetrafluoroethylene (PFA), fluorinated ethylene propylene (FEP), copolymers of tetrafluoroethylene (TFE) and polytetrafluoroethylene (PTFE). Several examples of a hydrophilic coatings include crosslinked polyacrylates, copolymers of acrylic acid, polymethacrylate, polyacrylamides, poly(vinyl alcohol), poly(ethylene oxide), poly(ethylene imine), carboxymethylcellulose, methylcellulose, poly(acrylamide sulphonic acid), polyacrylonitrile, and poly(vinyl pyrrolidone). Several examples of polyolefins include polyethylene and polypropylene. One skilled-in-the-art will recognize that other biomedical polymers exist that are suitable for use as a polymer overlay 55.

The hardness of the polymer overlay 55 disposed about the metal core 52 can affect the flexibility associated with the delivery member 15. Hardness is one of the more important physiomechanical characteristics of a material that influences the ability of the material to resist elastic and plastic deformation of the material's surface. The term adequately applies to the resistance of a material against deformation that arises from indentation, scratching, cutting, or bending phenomena. In general, the application of a load that induces a shear strain in a material can cause the various structural elements of the material to become displaced relative to one another. The degree or magnitude of this displacement depends upon the hardness exhibited by the material and the magnitude of the applied load. In other words, the hardness exhibited by a material is a composite of multiple contributing factors, such as yield strength, work hardening, tensile stress, and modulus, rather than a basic property of the material itself. Hardness can be readily measured using a variety of standard test methods known to one skilled-in-the-art, including but not limited to Shore, Brinell, Vickers, and Rockwell testing. The hardness of the polymer overlay 55 can be predetermined and varied by modifying the contributing factors described above or through the incorporation of various types and amounts of inert filler materials, such as glass, silicon dioxide, and aluminum oxide, into the polymer overlay 55.

The delivery member 15 can be made with a uniform diameter (d) throughout its elongated traverse length. When desired to enhance the flexibility of the distal portion 25 of the delivery member 15, the distal portion 25 as a whole or in specific locations may exhibit a diminishing wall thickness (T) associated with the wire strands 50A in the metal core 52. Such a distal portion 25 may be fabricated by machining or grinding a region of the wire strands 50A to a desired thickness dimension after they are helically wound into the metal core 52.

This machined region can extend along the entire length of the delivery member 15, so that the delivery member 15 may exhibit a very precise outer dimension overall. In another aspect of the present invention, the machined region is part of the distal portion 25 of the delivery member 15. In this case, the machined region may be tapered, i.e., diameter decreases, which allows the device to exhibit increasing flexibility as one moves towards the distal end 30 of the delivery member 15.

This increased level of flexibility in the distal portion 25 of the delivery member 15 facilitates the introduction of the delivery member 15 into very diminutive vessels. The reduced cross-sectional area of the wire strands 50A produced by the machining operation greatly increases the bending flexibility of the medical device 10 without sacrificing its ability to transfer torque.

As an alternative or supplement to grinding, the delivery member 15 may be composed of several segments in which the wires have mutually different thicknesses (T). However, the cross-sectional area of the lumen is maintained substantially similar between the different segments in order to prevent the occurrence of any obstruction to the advancement of a guide wire or other device through the lumen. The different segments may be joined together in axial extension by laser welding, soldering, bracing, or any other method known to one skilled-in-the-art.

The distal portion 25 of the delivery member 15 may also be tapered towards its distal end 30 in order to enhance an interaction with a guide wire. The taper can either be restricted to the distal end 30 or extend along any desired length of the distal portion 25 of the delivery member 15. Due to this taper, the distal portion 25 will benefit from gradually increasing transverse flexibility and a higher degree of softness.

In order to make the distal end 30 of the delivery member 15 more visible to enhanced fluoroscopy, the distal end 30 may optionally include some type of radiopaque material, such as gold, platinum, iridium, palladium, or rhodium, or a mixture thereof. If desired, the radiopaque material can be of annular shape located at a predetermined distance from the distal end or the distal end 30 of the delivery member 15 can be provided with a marker means for making it radiopaque, such as a gold layer or a gold thread.

The leak-free connector 40 may be selected as any vacuum fitting or fluid fitting known to one skilled-in-the-art. Preferably the leak-free connector 40 is a Luer-taper fitting, such as a Luer-Lok or Luer-Slip fitting. A Luer-Lok fitting utilizes a tabbed hub on the female portion of the fitting to engage threads positioned on the sleeve of the mating male portion of the fitting in order to achieve leak-free behavior. A Luer-Slip fitting typically utilizes frictional forces to maintain connectivity throughout the tapered fitting.

By making the metal core 52 from a group of at least five wire strands 50A that are helically wound with a pitch angle roughly corresponding to the aggregate width of the adjacent strands 50A, the strands 50A transfer torque and also force components directed in the axial direction of the delivery member 15, i.e., from the proximal end 35 to its distal end 30. Thus the delivery member 15 exhibits a very high resistance to kinking and less concentration of transmitted forces in areas where the delivery member bends due to the influence of the vascular walls.

Due to the flexibility, pushability, and ability to transmit torque, as well as the ability of the delivery member 15 to maintain each of these three characteristics the medical device 10 can be used with very small and distant vessels, such as deep brain sites accessed by intracranial catheterization. In addition, the delivery member 15 of the present invention exhibits a more pronounced ability to transfer torque, low windup, whip, pushability, and use tension as other commonly used unifilar or multifilar coiled cannulas without sacrificing compression strength, hoop strength, or thin wall thickness.

In one embodiment of the present invention, the group or row of wires is made up of from about 5 to 12 helically wound wires, preferably from 6 to 9 helically wound wires. Since several wires are used, their aggregate width can be adapted to correspond to the desired pitch for the given diameter of the device. A row of more than 12 wires would have a tendency to buckle when the wires are helically wound in a conventional winding operation.

In order to promote uniform and well-defined characteristics along the entire length of the medical device 10, the wire strands 50A when positioned in a row are preferably located closely next to each other so that they can mutually contact and support each other. Any possible deflection of a single wire strand 50A is therefore reduced to a minimum by the others strands 50A located in the row. As the wires in the row are helically wound in a common movement a slight interstice can exist between the turns of the row of wires. The inside surface of the metal core 52 of the present invention is found to be consistent, thereby, promoting the axial advancement of a guide wire or other device through the delivery member 15. The capabilities of torque and push are presumably a result of the mutual interlocking of the individual wire strands 50A wound into the metal core 52. If one strand 50A has a tendency to kink or bend when a load is applied to the delivery member 15, the other wire strands 50A will keep this strand in place due to the existence of a common helical path that interlocks this strand with the other strands 50A.

In one embodiment of the present invention, the wire strands 50A have a pitch angle in the range of about 25° to 77°, preferably a pitch angle in the range of 40° to 65°. Although it is possible to use other pitch angles, angles chosen in these ranges provide a balanced solution to the requirements for desired high flexibility, high column strength, and fine torqueability. The preferred range of 40° to 65° is useful for advancing a catheter through small sized vessels, such as in blood vessels in the brain. On the other hand, a pitch angle in the range of about 35° to 40° is useful when a very high degree of flexibility is required. A pitch angle in the range of about 70° to 75° is useful when the application calls for a very high amount of pushability. One skilled-in-the-art will realize that it is possible to choose different pitch angles in different segments of the delivery member 15.

The wire strands 50A are to a large extent mutually locked in position because the strands 50A are wound and drawn together. Thus one wire strand 50A is kept in place by the other strands 50A. However, some mutual movement can occur between the wire strands 50A. The polymer overlay 55 is useful in sealing any interstice that may exist between the wire strands 50A, thereby, rendering the delivery member 15 leak-proof. The elasticity of the polymer overlay 55 allows small mutual movements of the wire strands 50A to occur, thereby, imparting excellent flexibility to the helically wound metal core 52.

It is preferable that the distal portion 25 of the delivery member 15 be at least 30 cm in length with the maximum outer diameter of said distal portion being less than 2.0 mm. The maximum outer diameter of the delivery member 15 has a profound effect on suitable application of the medical device 10. An outer diameter of less than about 1.00 mm allows the introduction of the delivery member 15 into fine, diminutive vessels, such as the external and internal carotid arteries. An outer diameter less than about 0.75 mm allows an operator to advance the delivery member into the liver and other soft tissue areas. An outer diameter less than about 0.30 mm in at least the last 10 cm length of the distal portion 25 before the distal end 30 makes distant vascular regions accessible allowing the delivery member 15 to be used as a neuro-microcatheter.

Individual features of the various embodiments can be combined into further embodiments according to the present invention. It is possible to deposit the polymer overlay 55 as a multilayer coating, e.g., a coating comprising a primer-coating and a top-coat where the primer-coating is chosen to provide strong bonding to the wire strands 50A, and the top-coat providing the sealing and acting as a hydrophilic, low friction surface.

Figure 7:
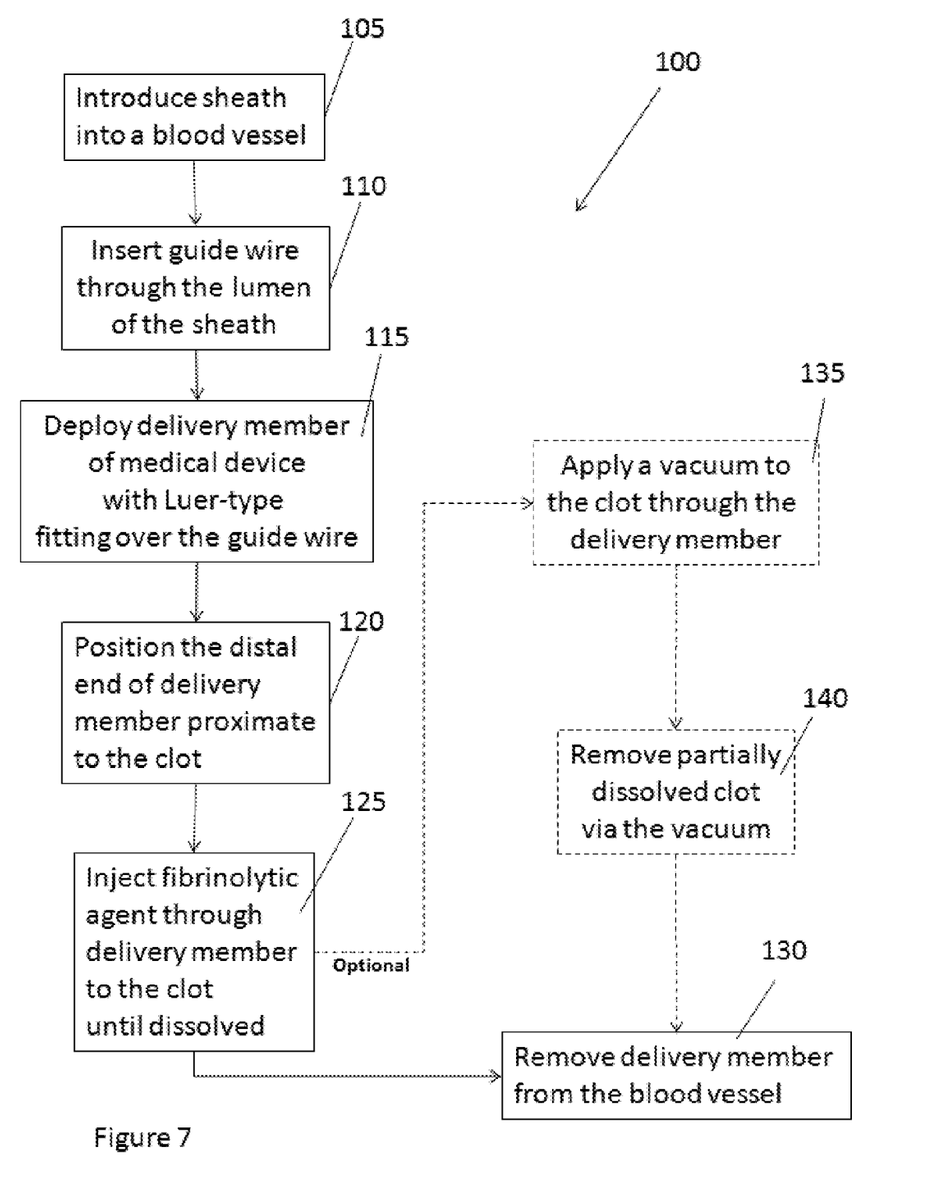
FIG. 7 is a schematical representation of a method for using the medical device of FIG. 1 for the removal of emboli according to the teachings of the present invention.

Another objective of the present invention is to provide a method for performing fibrinolysis by chemical infusion and/or the vacuum removal of emboli present in a vasculature of a patient. In FIG. 7, a method of addressing fibrin clots formed in a small vessel, such as an intracranial vasculature, is shown according to the teachings of the present invention. This method comprises the steps of introducing a sheath having a lumen into a blood vessel; inserting a guide wire through the lumen of the sheath; deploying the elongated tubular delivery member of a medical device having distal and proximal portions with a common lumen over the guide wire into the blood vessel; positioning the distal end of the delivery member proximate to a clot; removing the guide wire; injecting a fibrinolytic agent into the blood vessel through the delivery member until the clot is dissolved; and removing the delivery member of the medical device from the blood vessel.

The delivery member 15 of the medical device 10 has a metal core 52 comprising multiple shaped-wire strands 50A having an A-side 47 and a B-side 48, the wire strands 50A helically wound to form a lumen 45 with its inner diameter being defined by the A-side 47 of the strands and a polymer overlay 55 disposed about the B-side 48 of the metal core 52; said helically wound wire strands 50A further forming a first polygon 70 defined by the B-side 48 of the strands and a second polygon 75 defined by the A-side 47 of the strands 50A; the second polygon 75 defining the shape of the lumen 45. The medical device 10 further comprising a connector 40 engaged with the proximal portion of the delivery member 15. The connector 40 being compatible for use with fibrinolytic agents, application of a vacuum, or both.

The step of positioning the delivery member proximate to the clot can be accomplished due to the rigidity of the proximal portion being greater than the rigidity of the distal portion. The step of injecting a fibrinolytic agent into the blood vessel through the delivery member until the clot is dissolved is facilitated by the metal core having an inside diameter that is less than about 1.25 mm and an outside diameter that is greater than about 0.30 mm; with the ratio of the inside diameter to the outside diameter being greater than about 1.5.

The method 100 may further comprise the steps of applying a vacuum to through the delivery member to a clot that is only partially dissolved and removing the partially dissolved clot via the vacuum.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A medical device for clot removal from small vessels by fibrinolytic infusion or vacuum retrieval, the device comprising:
    an elongated tubular delivery member having a proximal portion and a distal portion, the delivery member comprising a metal core of multiple shaped-wire strands having an A-side and a B-side, the wire strands helically wound to form a lumen with an inner diameter defined by the A-side of the strands and a polymer overlay disposed about the metal core; the proximal portion and distal portion being different in their predetermined degree of rigidity; and
    a leak-free connector in contact with the proximal portion of the delivery member; the connector being compatible for use with fibrinolytic infusion and vacuum retrieval;
    wherein the helically wound wire strands form a first polygon defined by the B-side of the strands and a second polygon defined by the A-side of the strands; the second polygon defining the shape of the lumen.

2. The device of claim 1, wherein the first polygon inscribes a first circle having a radius, $R_1$, and the second polygon circumscribes a second circle having radius, $R_2$;
    wherein the difference in magnitude between $R_1$ and $R_2$ is about equal to the thickness of the wire strands.

3. The device of claim 2, wherein the ratio of the area (A1) of the first polygon to the area (A2) of the second polygon is about equal to the quotient of:

$$[(R_1)^2 \cdot \cos^2(\pi/N)]/(R_2)^2,$$

where N is the number of wire strands.

4. The device of claim 1, wherein the difference in rigidity of the proximal and distal portions of the delivery member results from a variation in one of the wall thickness of the metal core, the hardness of the overlay, and a combination thereof.

5. The device of claim 1, wherein the shape of the wire strands that form the metal core is selected as one from the group of half round shaped D-wire, less than half round shaped D-wire, pie angle shaped wire with greater than about a 100° degree angle, triangular shaped wire having an obtuse angle, rectangular shaped wire, square shaped wire, flat shaped wire, crescent shaped wire, and combinations thereof.

6. The device of claim 1, wherein the hollow metal core has an inside diameter that is less than about 1.25 mm and an outside diameter that is greater than about 0.30 mm.

7. The device of claim 6, wherein the ratio of the inside diameter to the outside diameter is greater than about 1.5.

8. The device of claim 1, wherein the metal core is made up of at least 5 shaped-wire strands.

9. The device of claim 1, wherein the hollow metal core comprises two layers of helically wound shaped-wire strands; the second layer being disposed about the first layer.

10. The device of claim 1, wherein the polymer overlay is one selected from the group of a coated material, an extruded material, and a shrink tubing material; with the composition of the material being one selected from the group of fluoropolymers, hyrdrophilic elastomers, polyolefins, and combinations or mixtures thereof.

11. The device of claim 1, wherein the leak-free connector is one selected from the group of a Luer-lock fitting and Luer-Slip fitting.

12. The device of claim 4, wherein the variation in wall thickness of the core results from a grinding operation being performed on the outer diameter of the core's distal portion.

13. The device of claim 4, wherein the variation in wall thickness of the hollow core results from using at least one different core for the proximal portion and the distal portion that have substantially similar inner diameters, but different outer diameters;

wherein the distal end of the core used in the proximal portion of the delivery member and the proximal end of the core used in the distal portion of the delivery member are in contact with one another such that their inner diameters engage one another.

14. The device of claim 1, wherein the rigidity of the proximal portion is greater than the rigidity of the distal portion.

15. The device of claim 1, wherein the distal portion further comprises a distal end in which the inner diameter of the delivery member is tapered to contact and retrievably receive a guide wire.

16. The device of claim 1, wherein the multiple shaped-wire strands are helically wound with a pitch angle ($\alpha$) between about 25 to 77 degrees.

17. The device of claim 1, wherein the distal portion of the delivery member further comprises a radiopaque material to enhance visibility during fluoroscopy; the radiopaque material being one selected from the group of gold, platinum, iridium, palladium, rhodium, and a mixture thereof.

18. The device of claim 1, wherein the wire strands are each angled in the same direction relative to a longitudinal axis defined by the lumen.

19. The device of claim 18, wherein the wire strands are parallel to each other.

20. A medical device for clot removal from small vessels by fibrinolytic infusion or vacuum retrieval, the device comprising:

an elongated tubular delivery member having a proximal portion and a distal portion, the delivery member comprising a metal core of multiple non-braided shaped-wire strands having an A-side and a B-side, the wire strands helically wound to form a lumen with an inner diameter defined by the A-side of the strands and a polymer overlay disposed about the metal core; the proximal portion and distal portion being different in their predetermined degree of rigidity; and a leak-free connector in contact with the proximal portion of the delivery member; the connector being compatible for use with fibrinolytic infusion and vacuum retrieval;

wherein the helically wound wire strands form a first polygon defined by the B-side of the strands and a second polygon defined by the A-side of the strands; the second polygon defining the shape of the lumen.

* * * * *